(12) United States Patent
Botich et al.

(10) Patent No.: US 7,753,887 B2
(45) Date of Patent: *Jul. 13, 2010

(54) RETRACTABLE NEEDLE MEDICAL DEVICE

(75) Inventors: Michael J. Botich, Reno, NV (US); John Barker, Ventura, CA (US); Thor R. Halseth, Agoura, CA (US)

(73) Assignee: MDC Investment Holdings, Inc., Salt Lake City, UT (US)

( * ) Notice: Subject to any disclaimer, the term of this patent is extended or adjusted under 35 U.S.C. 154(b) by 1606 days.

This patent is subject to a terminal disclaimer.

(21) Appl. No.: 10/401,426

(22) Filed: Mar. 28, 2003

(65) Prior Publication Data

US 2005/0075606 A1 Apr. 7, 2005

Related U.S. Application Data

(63) Continuation of application No. 09/744,923, filed on Apr. 17, 2001, now Pat. No. 6,547,762.

(51) Int. Cl.
*A61M 5/00* (2006.01)

(52) U.S. Cl. ............. 604/164.12; 604/110; 604/165.01; 604/164.01

(58) Field of Classification Search ............ 604/164.03, 604/164.13, 164.08, 164.09, 164.11, 164.12, 604/164.08–13, 110, 164.01, 165.01
See application file for complete search history.

(56) References Cited

U.S. PATENT DOCUMENTS

| | | | |
|---|---|---|---|
| 4,274,408 A | 6/1981 | Nimrod | |
| 4,958,622 A | 9/1990 | Selenke | |
| 4,994,042 A * | 2/1991 | Vadher | 604/165.01 |
| 5,045,065 A | 9/1991 | Raulerson | |
| 5,195,985 A | 3/1993 | Hall | |
| 5,353,808 A | 10/1994 | Viera | |
| 5,358,495 A | 10/1994 | Lynn | |
| 5,376,075 A | 12/1994 | Haughton et al. | |
| 5,380,290 A | 1/1995 | Makower et al. | |
| 5,514,100 A | 5/1996 | Mahurkar | |
| 5,575,777 A | 11/1996 | Cover et al. | |
| 5,579,780 A | 12/1996 | Zadini et al. | |
| 5,685,855 A | 11/1997 | Erskine | |
| 5,695,474 A | 12/1997 | Daugherty | |
| 5,697,907 A | 12/1997 | Gaba | |
| 5,702,367 A * | 12/1997 | Cover et al. | 604/110 |
| 5,704,914 A | 1/1998 | Stocking et al. | |
| 5,718,688 A * | 2/1998 | Wozencroft | 604/164.07 |

(Continued)

*Primary Examiner*—Nicholas D Lucchesi
*Assistant Examiner*—Laura A Bouchelle
(74) *Attorney, Agent, or Firm*—Rutan & Tucker, LLP

(57) ABSTRACT

A catheter insertion device is provided that includes an insertion needle that is retractable into the device after use to prevent exposure to the contaminated needle. The needle retainer releasably retains the needle in an extended position against the bias of the biasing element. When the catheter is removed from the insertion device, the needle retainer automatically releases the needle, which is propelled rearwardly into the device.

A device for inserting a guide wire into a patient is also provided. The device includes an insertion needle that is retractable into the housing of the device after use. A needle retainer releasably retains the needle in an extended position against the bias of the biasing element. After the guide wire is inserted into the patient, the needle retainer allows the needle to be released, so that the needle is retracted into the device.

13 Claims, 9 Drawing Sheets

U.S. PATENT DOCUMENTS

| | | |
|---|---|---|
| 5,749,371 A | 5/1998 | Zadini et al. |
| 5,795,339 A | 8/1998 | Erskine |
| 5,800,395 A * | 9/1998 | Botich et al. ................ 604/110 |
| 5,827,202 A | 10/1998 | Miraki et al. |
| 5,879,338 A | 3/1999 | Mahurkar |
| 6,547,762 B1 * | 4/2003 | Botich et al. ................ 604/110 |

* cited by examiner

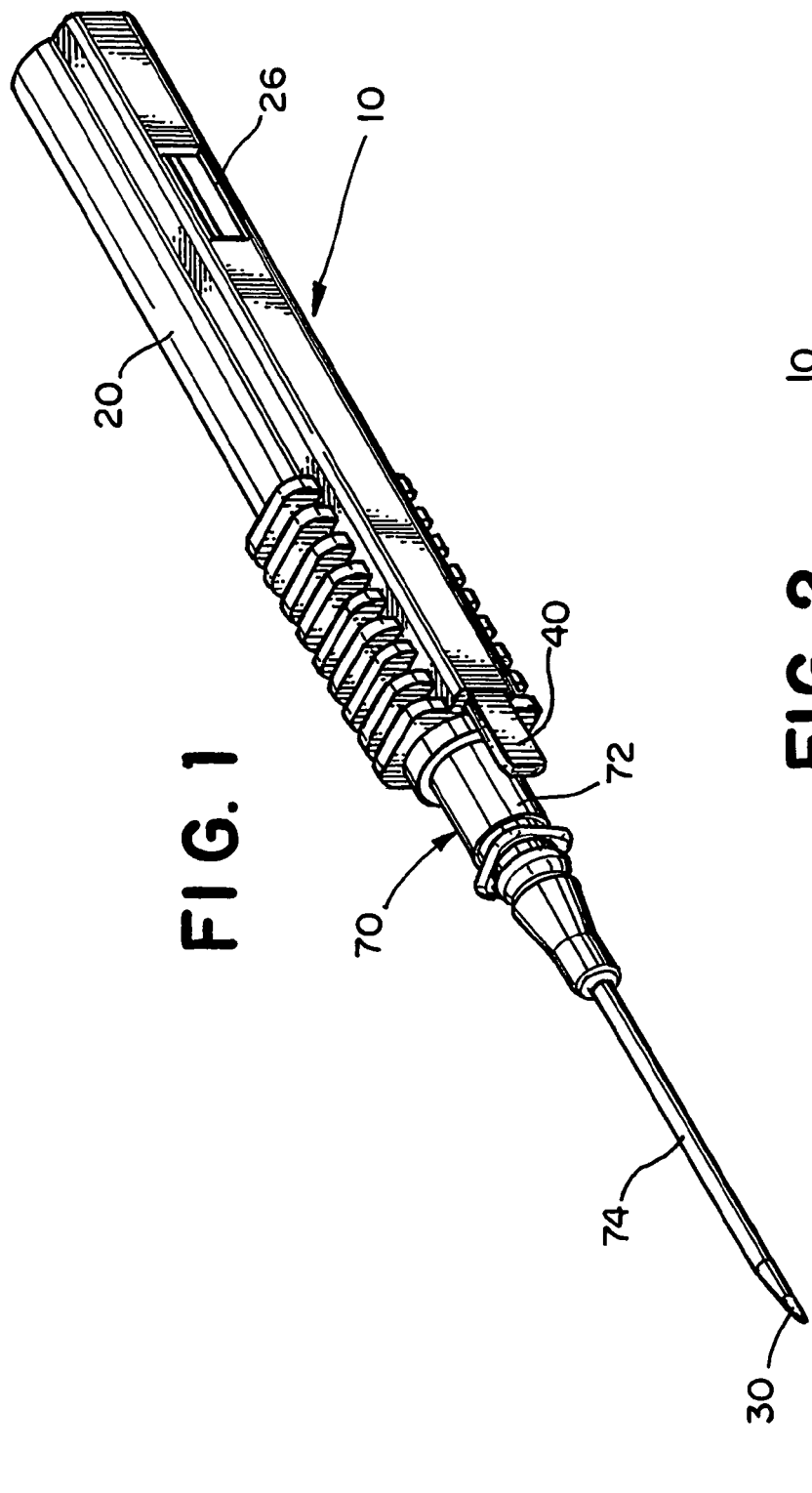
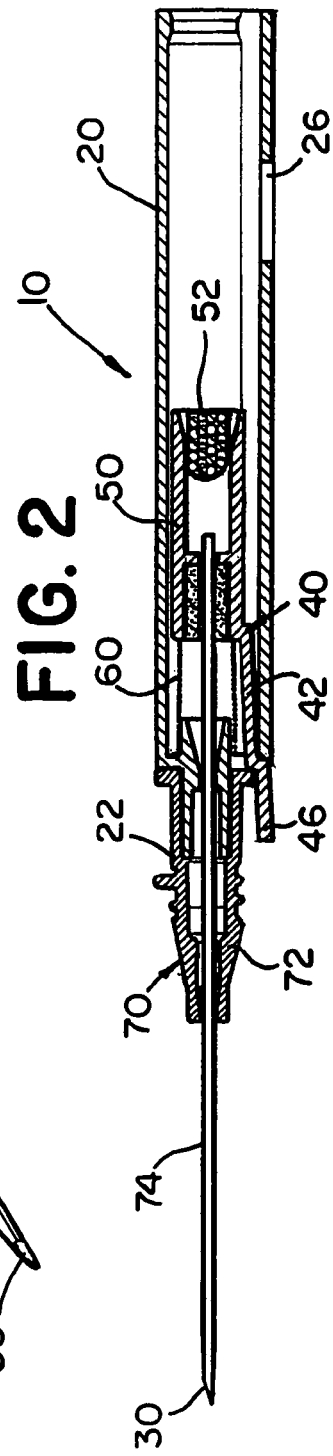

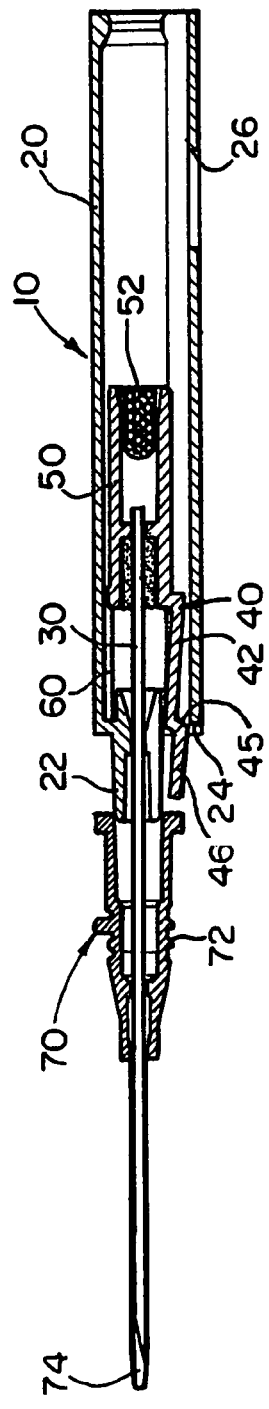
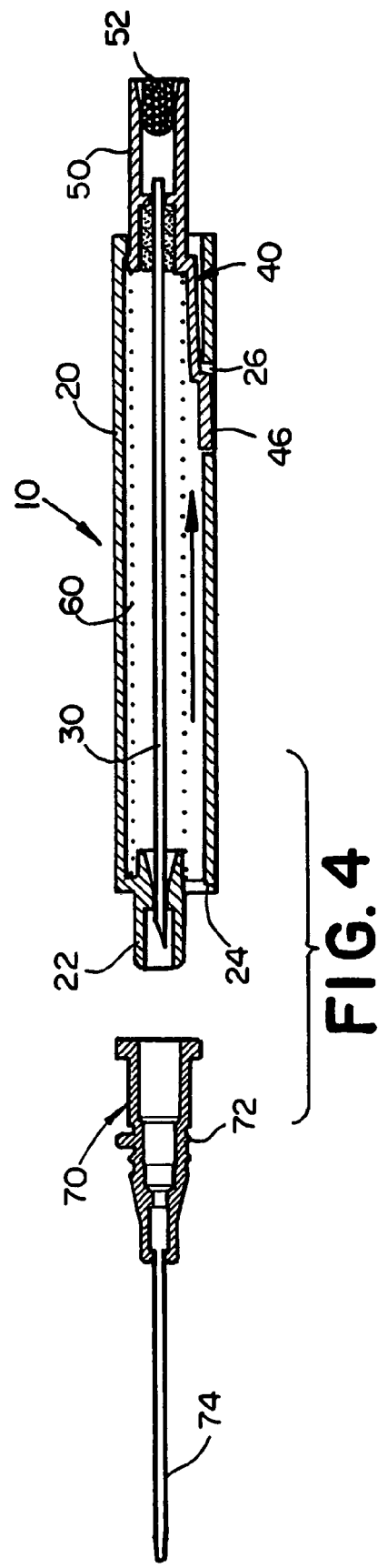

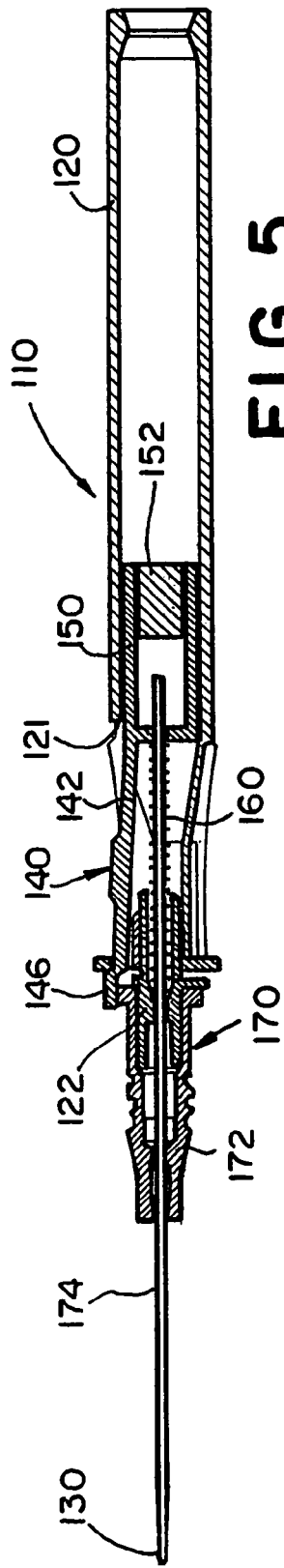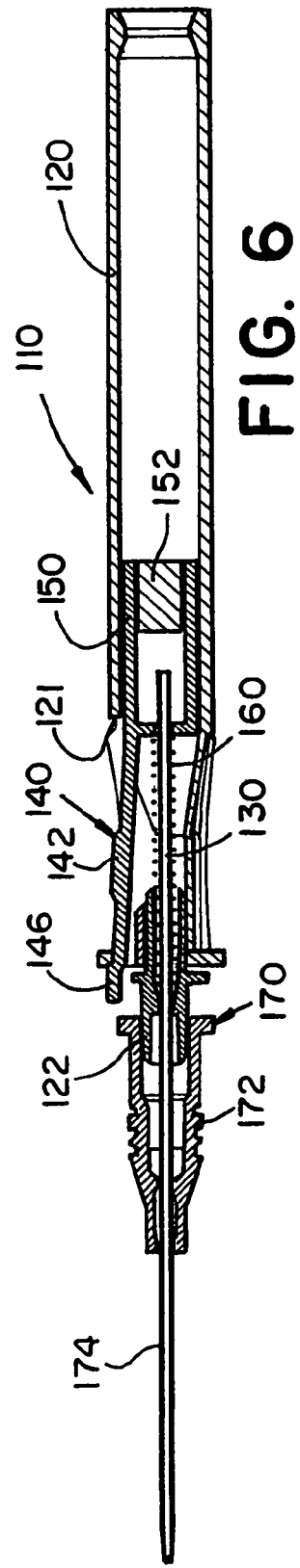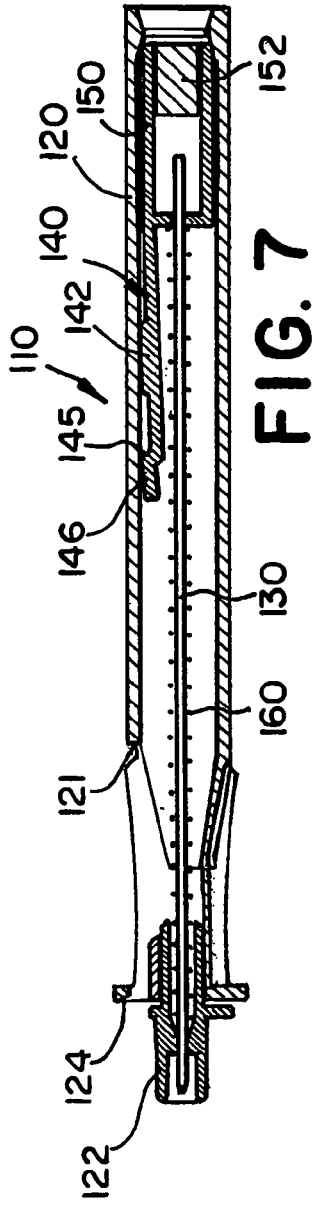

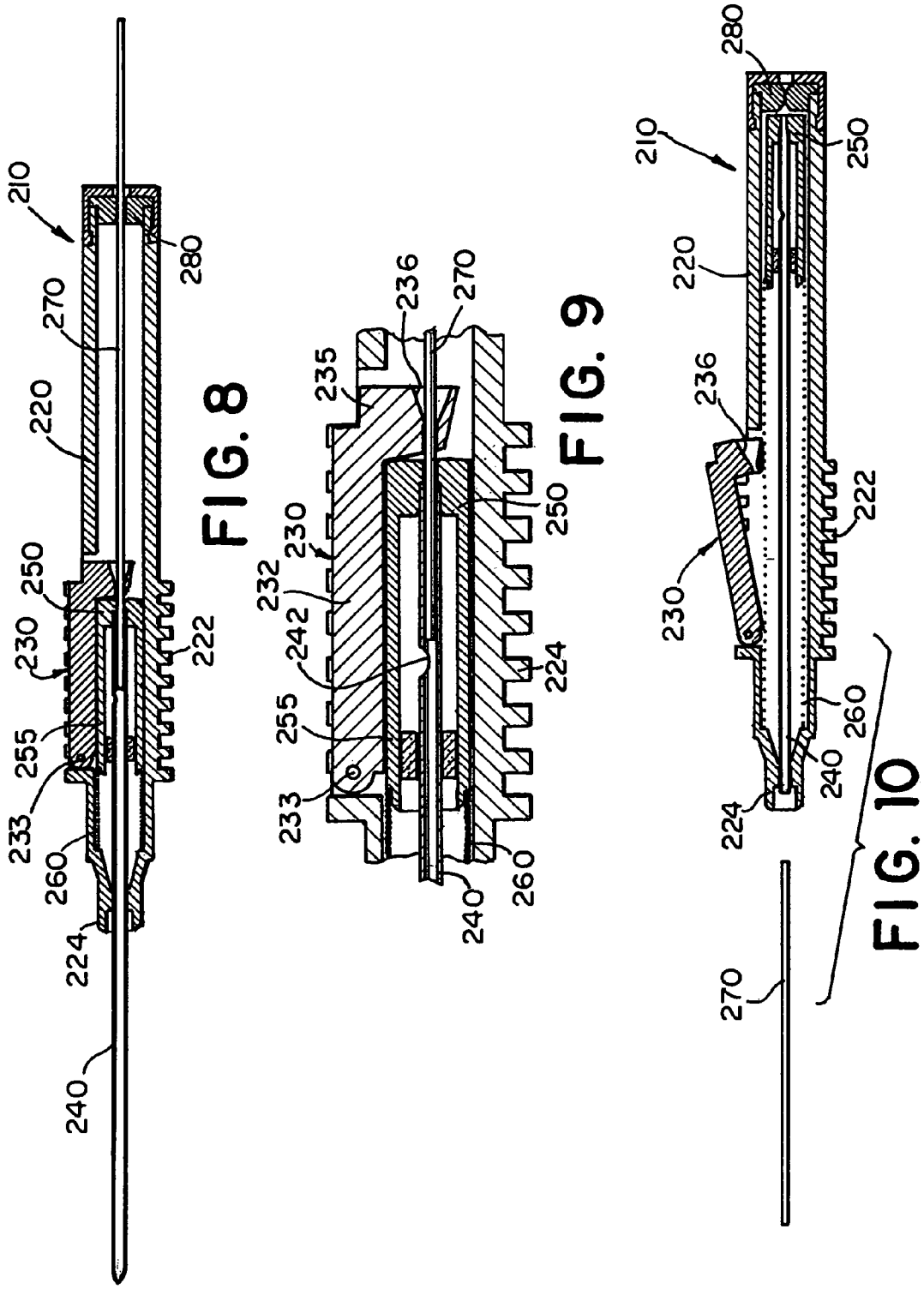

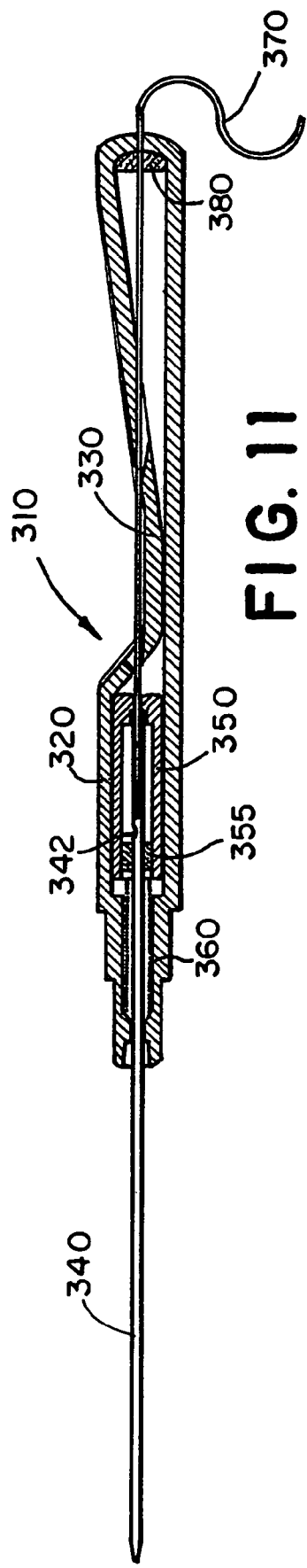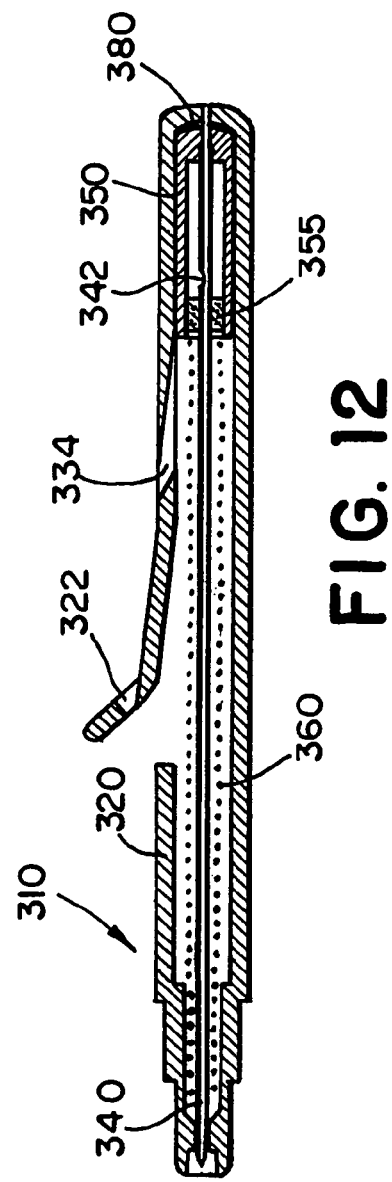

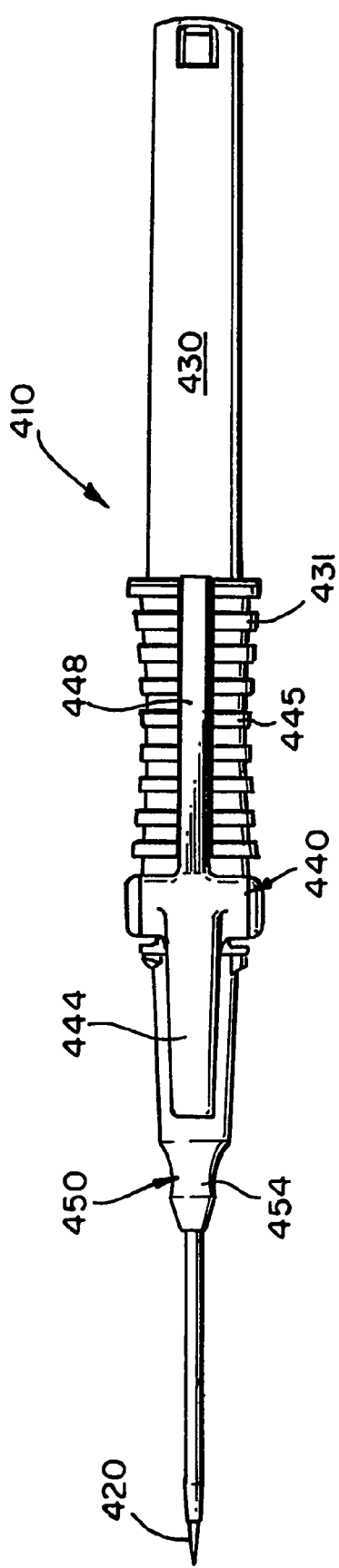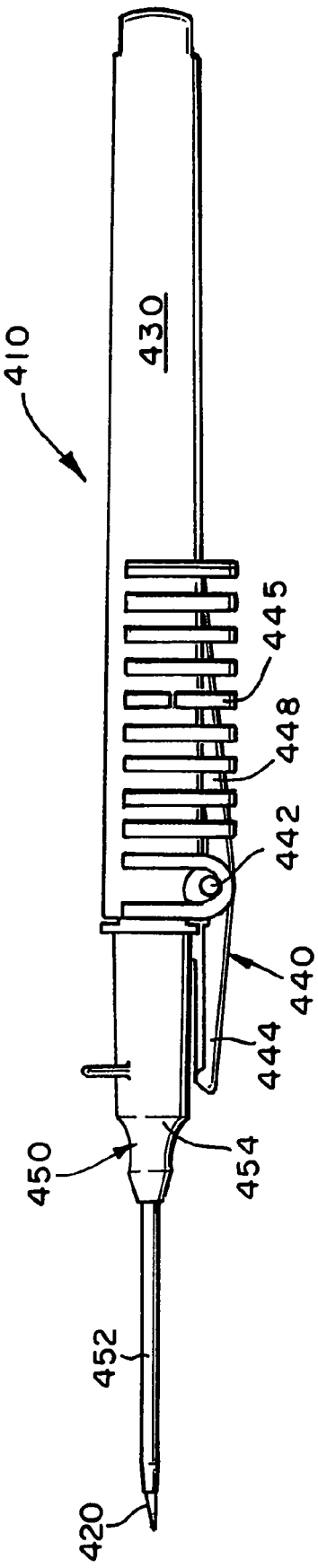
FIG. 14
FIG. 13

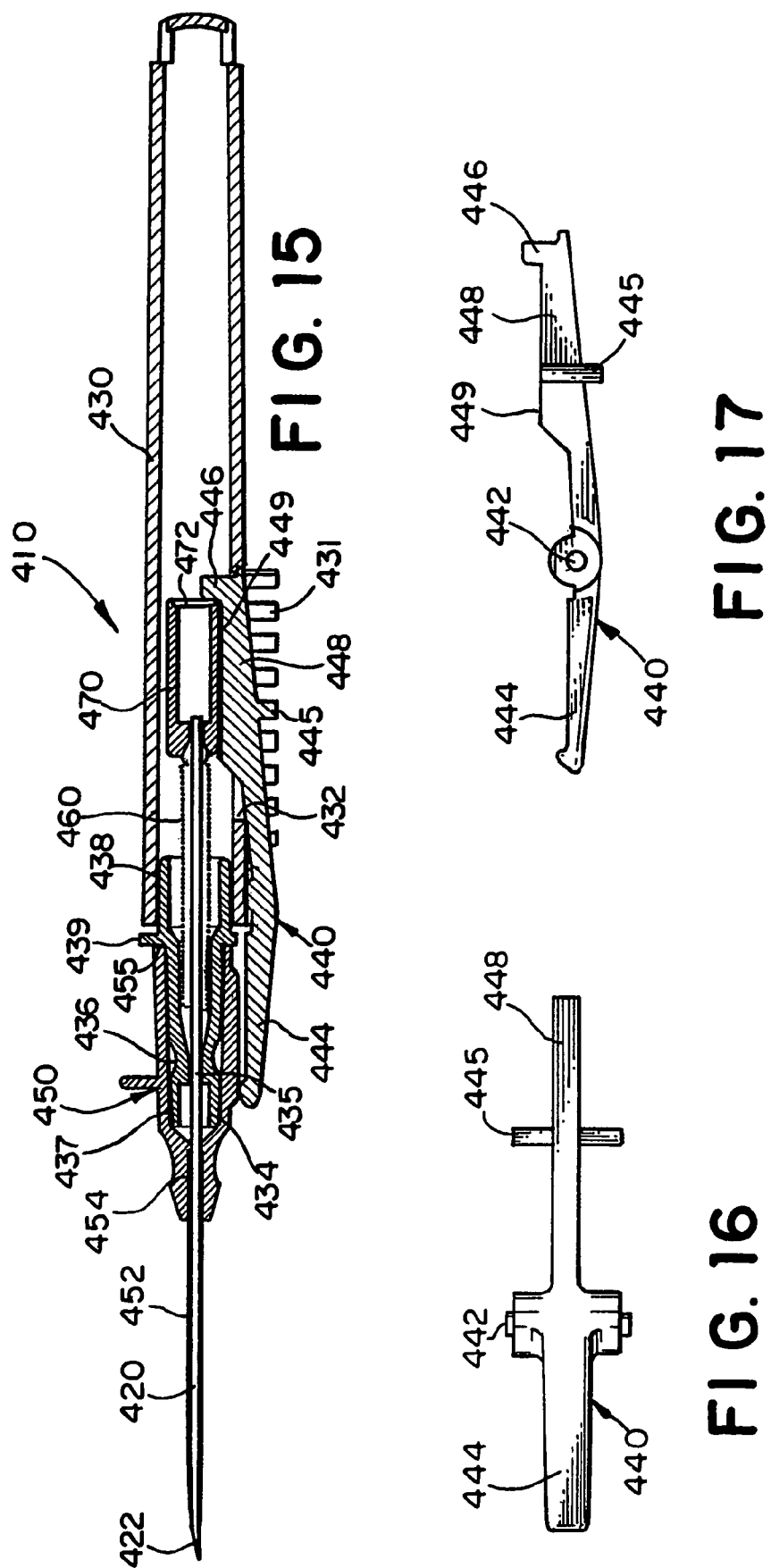

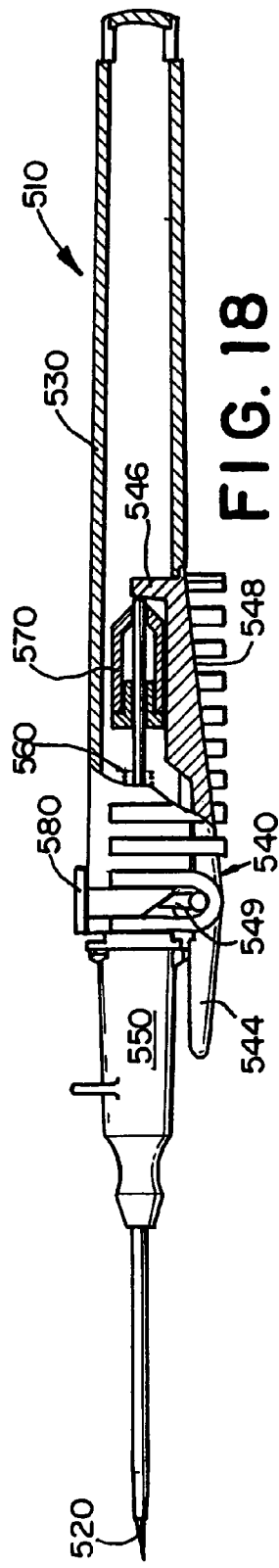
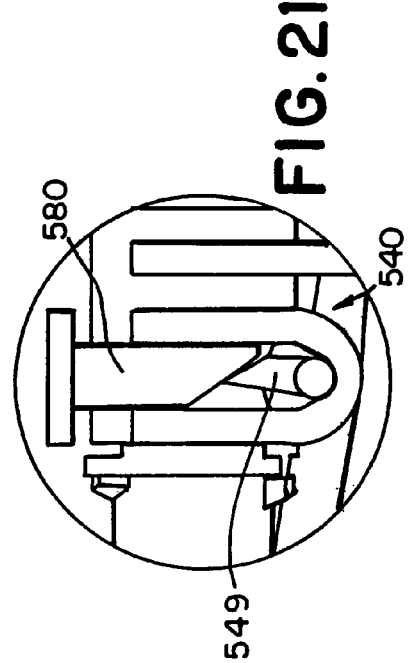
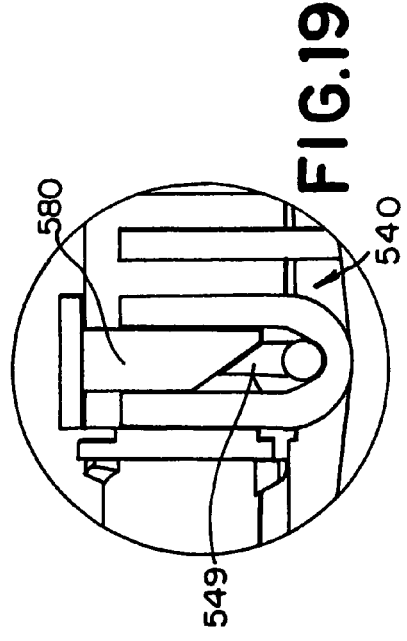
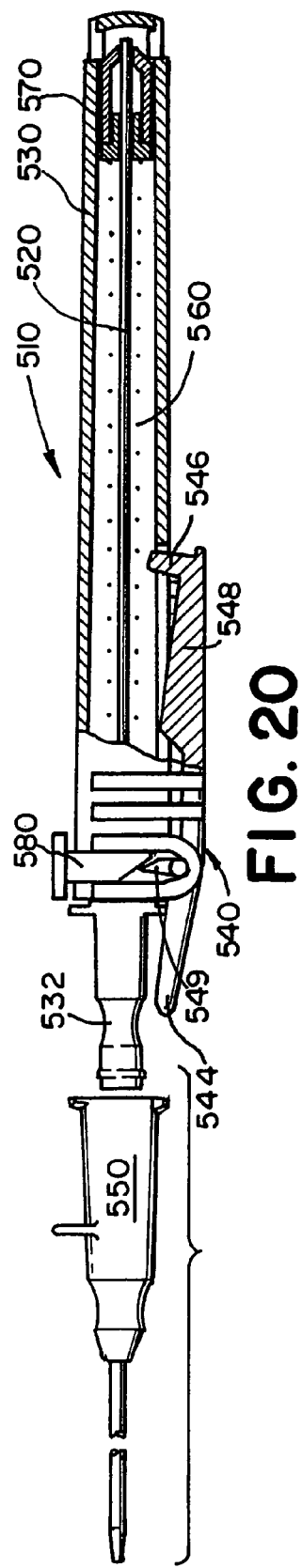

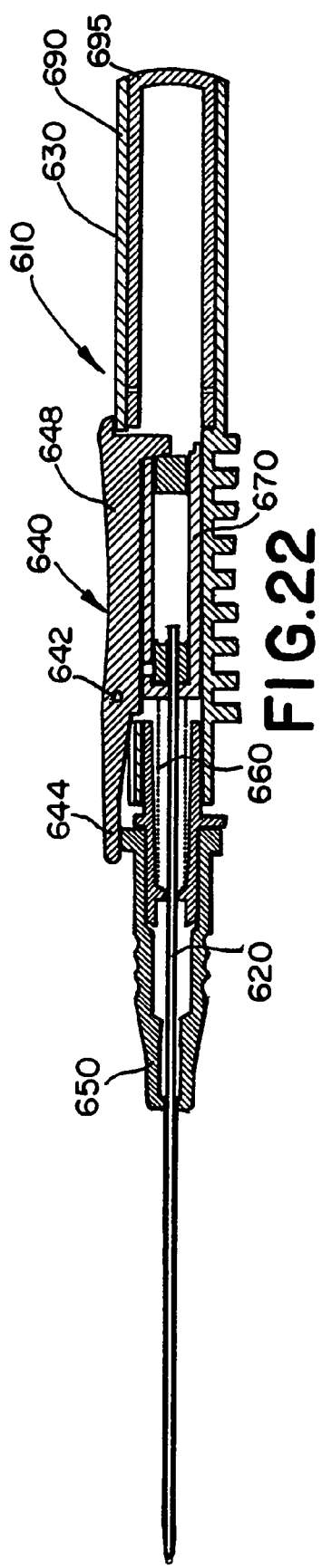
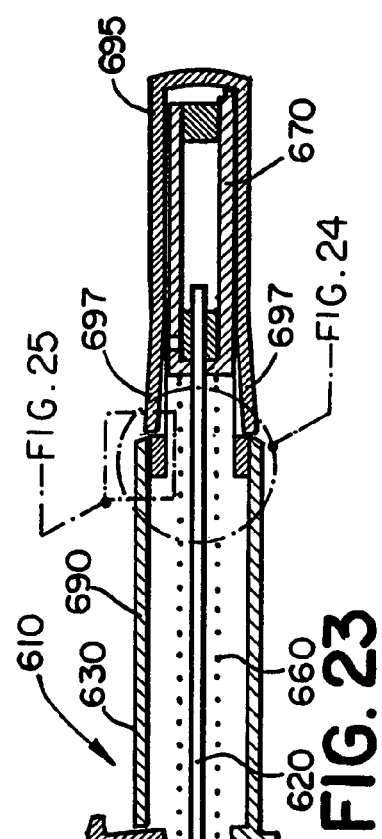
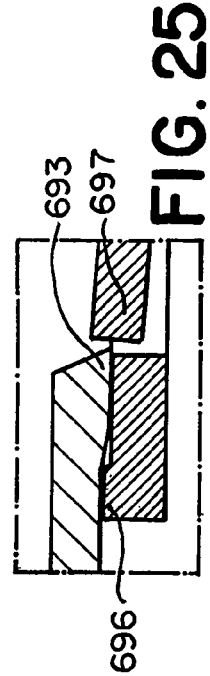
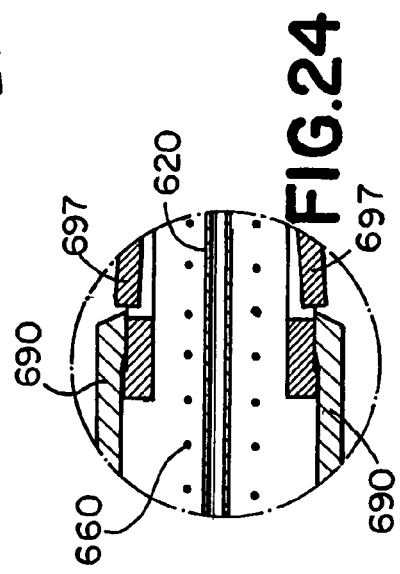

RETRACTABLE NEEDLE MEDICAL DEVICE

RELATED APPLICATIONS

This application is a continuation of U.S. application Ser. No. 09/744,923, filed Apr. 17, 2001, now U.S. Pat. No. 6,547,762 which is a Section 371 filing of International application No. PCT/US99/10609, filed May 13, 1999, which claims priority to U.S. Provisional Application No. 60/120,888 filed Feb. 20, 1999, U.S. Provisional Application No. 60/112,504 filed Dec. 14, 1998 and U.S. Provisional Application No. 60/094,801, filed Jul. 31, 1998. Each of the foregoing applications is hereby incorporated herein by reference.

FIELD OF THE INVENTION

The present invention relates to needle-bearing medical devices used, for example, to insert catheters or guide wires into blood vessels of patients. More specifically, the invention relates to such a device having a retractable needle feature for rendering the device non-reusable and safely disposable.

BACKGROUND

Various types of medical devices employed a needle for piercing the skin of a patient for diagnostic or therapeutic purposes. One such device is an intravenous catheter insertion device for positioning a needle mounted catheter into a patient's blood vessel. Another such device is the device for introducing a guidewire into a patient. The guidewire is then used to guide a catheter into the patient. Once the guidewire or catheter is properly positioned, the catheter insertion device is withdrawn leaving the guidewire or catheter in place in the blood vessel. Handling of such medical devices after the needle is withdrawn from the patient can result in transmission of various pathogens, most notably human immune virus (HIV), due to in inadvertent needle stick to medical personnel.

Since the mid-1980s, concern over the risk of accidental needle stick injuries has spawned a number of design approaches for safety needle devices. Such devices can be broadly categorized as either sliding sheath needle devices, wherein a physical barrier is positioned over the needle tip after use or as devices with needle retraction, wherein the exposed portion of the needle is retracted into the device after use. The latter category of needle retraction devices can be further subdivided into manual and semiautomatic retraction devices. Manual retraction devices, as exemplified by U.S. Pat. Nos. 4,026,287 to Haller, 4,592,744, to Jagger, 4,808,169 to Haber and 5,067,490 to Haber, require the user to pull or slide a needle-connected mechanism rearwardly to retract the needle into the device. In semiautomatic needle retraction devices, a biasing member, such as a spring, may be employed to push or pull the needle into the device in response to activation by the user of a release mechanism. Such devices are exemplified by U.S. Pat. Nos. 4,813,426 to Haber et al. and 5,125,414 to Dysarz.

U.S. Pat. No. 4,747,831 of Kulli and U.S. Pat. No. 4,900,307 of Kulli show respective catheter insertion devices and syringes with semiautomatic needle retraction. The retraction mechanism shown in the last-mentioned two patents are disclosed to be actuable by the user upon depression of a release button after the catheter is removed from the insertion device or the needle is removed from the patient.

The prior art semiautomatic devices require manual actuation by the operator. In many situations, such as an emergency situation, the operator is distracted or rushed so that the manual step necessary to effectuate retraction is not performed, either intentionally or unintentionally. In such instances, the used needle remains exposed, creating a risk of an inadvertent needle stick. Therefore, it would be desirable to provide an automatic needle retraction mechanism in which needle retraction is effectuated by normal operation of inserting the catheter into the patient, without the need to perform a separate manual step. It is further desirable to provide a device with a limited number of components so that the device can be produced cost effectively.

SUMMARY OF INVENTION

With the foregoing in mind, the present invention provides a medical device having a hollow housing and a catheter mounted on the housing. The device includes a needle operable between an extended position extending forwardly from the housing and a retracted position in which the needle is enclosed in the housing. A biasing element biases the needle toward the retracted position. A needle retainer is fixedly connected with the needle. The needle retainer releasably retains the needle in the extended position against the bias on the biasing element. The needle retainer preferably comprises an elongated arm having a follower portion engaging the catheter. Upon removal of the catheter from the housing, the catheter disengages the follower portion, thereby allowing the needle retainer to release the needle. The biasing element then propels the catheter rearwardly into the housing.

The present invention also provides a medical device having a hollow housing and a needle for inserting a guidewire. The device includes a needle operable between an extended position extending forwardly from the housing and a retracted position in which the needle is enclosed within the housing. A biasing element biases the needle toward the retracted position. The device includes a needle retainer operable between a first position in which the needle retainer releasably engages the needle against the rearward bias of the biasing element, and a second position in which the needle retainer releases the needle allowing the biasing element to displace the needle into the retracted position. The guidewire engages the needle retainer to impede the needle retainer from displacing into the released position. After the guidewire is threaded into the patient, the needle retainer is displaced into the released position, and the biasing element propels the needle rearwardly into the housing.

The present invention also provides a method for inserting a medical apparatus carried by a needle, such as an intravenous catheter or guidewire. The method includes the step of providing an insertion device having a housing, a needle and a needle retainer for releasably retaining the needle so that the needle projects forwardly from the housing. The medical apparatus is inserted into the patient via the needle. The operator selectively manually engages the needle retainer to impede retraction of the needle. The operator then releases the selective manual engagement with the needle retainer to release the needle. The needle is then retracted into the housing.

DESCRIPTION OF DRAWINGS

The foregoing summary as well as the following detailed description of the preferred embodiments of the present invention will be better understood when read in conjunction with the appended drawings, in which:

FIG. 1 is a perspective view of a catheter insertion device having a retractable needle;

FIG. 2 is a cross-sectional view of the device shown in FIG. 1;

FIG. 3 is a cross-sectional view of the device shown in FIG. 2, illustrating the device with the catheter removed prior to retraction of the needle;

FIG. 4 is a cross-sectional view of the device shown in FIG. 2, illustrating the device after retraction of the needle;

FIG. 5 is a cross-sectional view of an alternate embodiment of a catheter insertion device having a retractable needle;

FIG. 6 is a cross-sectional view of the device shown in FIG. 5, illustrating the device with the catheter removed prior to retraction of the needle;

FIG. 7 is a cross-sectional view of the device shown in FIG. 5, illustrating the device after retraction of the needle;

FIG. 8 is a side elevational view of a retractable needle device for introducing a guide wire into a patient;

FIG. 9 is an enlarged fragmentary sectional view of the guide wire introduction device illustrated in FIG. 8;

FIG. 10 is a side view of the guide wire introduction device illustrated in FIG. 8, illustrating the needle in a retracted position;

FIG. 11 is a side elevational view of a second embodiment of a retractable needle device for introducing a guide wire into a patient;

FIG. 12 is a side view of the guide wire introduction device illustrated in FIG. 11, illustrating the needle in a retracted position;

FIG. 13 is a side elevational view of a catheter insertion device with a retractable needle according to the present invention;

FIG. 14 is a bottom plan view of the catheter insertion device illustrated in FIG. 13;

FIG. 15 is a sectional view of the catheter insertion device illustrated in FIG. 13;

FIG. 16 is a bottom plan view of a needle retainer of the catheter insertion device illustrated in FIG. 13;

FIG. 17 is a side elevational view of the catheter insertion device illustrated in FIG. 16;

FIG. 18 is a side elevational view partially in section of an alternate embodiment of a catheter insertion device with a retractable needle according to the present invention;

FIG. 19 is an enlarged fragmentary view of the catheter insertion device illustrated in FIG. 18, illustrating a locking button in a locked position;

FIG. 20 is a side elevational view partially in section of the catheter insertion device illustrated in FIG. 18, showing the needle in a retracted position;

FIG. 21 is an enlarged fragmentary view of the catheter insertion device illustrated in FIG. 20, illustrating the locking button in an unlocked position;

FIG. 22 is a sectional view of a second alternate embodiment of a catheter insertion device with a retractable needle according to the present invention;

FIG. 23 is a sectional view of the catheter insertion device illustrated in FIG. 22, illustrating the needle in a retracted position;

FIG. 24 is an enlarged fragmentary sectional view of the catheter insertion device illustrated in FIG. 23; and FIG. 25 is an enlarged fragmentary sectional view of the catheter insertion device illustrated in FIG. 23.

DETAILED DESCRIPTION OF THE PREFERRED EMBODIMENTS

Referring now to the FIGS. 1-4 in general and to FIG. 1 specifically, a device for inserting an over-the needle catheter 70 into a patient is designated generally 10. The device 10 includes a retractable needle 30 for piercing the skin of the patient to insert the catheter 70. After the catheter 70 is inserted into the patient, the needle 30 automatically retracts into the device 10 so that the sharpened tip of the contaminated needle is enclosed within the device to prevent inadvertent needle sticks.

Referring to FIGS. 2-4, the device includes a generally cylindrical housing 20, the needle 30, a spring 60 biasing the needle rearwardly, and a needle retainer 40 releasably retaining the needle against the bias of the spring. The needle is operable between two positions, a projecting position and a retracted position. In the projecting position, the needle 30 projects forwardly from the forward end of the housing 20. In the retracted position, the needle is retracted into the housing so that the sharpened tip is enclosed within the housing to prevent inadvertent contact with the sharpened tip. When the needle is in the projecting position, as shown in FIG. 2, the spring biases the needle rearwardly toward the retracted position. The needle retainer releasably retains the needle in the projecting position, against the bias of the spring. The needle retainer cooperates with the catheter 70, so that when the catheter is removed from the device the needle retainer automatically releases the needle and the needle retracts into the housing, as shown in FIG. 4.

Referring now to FIG. 2, the elements of the device will be described in greater detail. The housing is generally cylindrical and the forward end of the housing 20 has a reduced diameter tapered nose 22. The catheter 70 is mounted on the nose 22. Accordingly, the nose 22 is tapered to cooperate with the internal taper of the hub 72 of the catheter 70.

The catheter 70 includes a generally conical hub 72 and a flexible cannula 74 fixedly connected to the catheter hub. The catheter 70 is mounted on the nose 22 of the housing so that the cannula 74 sheaths the forward end of the needle. However, the sharpened tip of the needle projects forwardly from the cannula so that the sharpened tip is exposed prior to use.

When the catheter 70 is mounted on the nose 22, the catheter hub 72 engages the needle retainer 40. The needle retainer 40 is an elongated arm fixedly connected with the needle 30. The arm projects forwardly through an opening in the forward end of the housing, adjacent the tip. The forward portion of the arm 40 forms a follower portion 46. The follower portion projects forwardly from the housing, through the opening in the housing adjacent the nose 22 and engages the catheter hub 72.

The needle retainer 40 includes a ridge 45 that protrudes radially outwardly, rearwardly of the follower portion 46. The ridge 45 engages a lip 24 formed by the opening through which the arm 40 projects adjacent the nose. The ridge 45 operates as a latch to retain the needle retainer and the attached needle against the bias of the spring.

When the catheter 70 is mounted on the nose 22, the catheter hub 72 engages the follower portion 46 of the needle retainer 40 so that the ridge 45 is wedged into engagement with the lip 24. In this way, when the catheter is mounted on the device, the needle 30 is maintained in the projecting position against the bias of the needle. Removing the catheter 70 allows the needle retainer to deflect radially inwardly disengaging the ridge from the lip. In the present instance, the rearward bias of the spring radially deflects the needle retainer when the catheter is removed.

The needle retainer arm is formed of a flexible plastic so that the arm is resiliently deformable. In its relaxed state, the needle retainer arm 40 is disposed into engagement with the lip 24 of the forward opening. Preferably, the lip 24 is tapered rearwardly and the ridge 45 on the needle retainer 40 forms a mating tapered surface. These mating surfaces can be seen most clearly in FIGS. 3 and 4. Configured in this way, the rearward axial biasing force of the spring acts upon the arm in the form of a radial force component and an axial force component. The radial force component urges the needle retainer arm 40 inwardly so that the ridge 45 rides up and over the lip 24 until the ridge is out of engagement with the lip. The spring 60 then propels the needle retainer and the attached needle rearwardly into the housing so that the sharpened tip of the needle is enclosed within the housing.

The device 10 further includes a fluid reservoir 50 attached to the rearward end of the needle, enclosing the rearward end of the needle. The fluid reservoir 50 is in fluid communication with the needle 30 and operates as a flashback chamber. Accordingly, when the needle is inserted into a patient's vein, blood flows through the needle into the flashback chamber. The rearward end of the flashback chamber 50 is sealed by a porous hydrophobic vent plug 52. Air passes though the vent plug to allow air to pass out of the flashback chamber when the blood enters the flashback chamber. However, the vent plug 52 is not permeable to blood to prevent blood from leaking out of the flashback chamber. The housing and the flashback chamber are formed of translucent plastic so that the blood in the flashback chamber serves as a visible indicator that the needle is properly inserted into the patient's vein.

In the present instance, the flashback chamber 50 and the needle retainer 40 are integrally formed as a unitary structure. The two elements are fixedly attached to the needle by an adhesive such as UV curable epoxy. The spring is disposed within the housing, circumscribing the needle. The forward end of the spring bears against the forward end of the housing, the other end of the spring bears against the integral needle retainer and flashback chamber.

In the present instance, the housing 20 is shorter than the combined length of the needle 30 and the flashback chamber 50. Accordingly, the rearward end of the housing 20 is generally open, allowing the flashback chamber to project rearwardly out of the housing when the needle is retracted, as shown in FIG. 4. The device also includes a locking or limiting feature to ensure that the needle is not propelled rearwardly out of the housing. Preferably, an aperture 26 sized to receive the forward portion 46 of the needle retainer arm 40 is formed in the side of the housing operates as the rearward lock. The resilience of the needle retainer biases the needle retainer radially outwardly. When the needle is propelled rearwardly, the forward end of the needle retainer 46 engages the aperture 26 so that the ridge 45 engages the rearward edge of the aperture, retaining the needle against continued rearward displacement. In addition, the forward end of the needle retainer 40 engages the forward edge of the aperture 26 to retain the needle against forward displacement, so that the needle cannot be re-extended after it is retracted.

When the catheter 70 is removed from the device and inserted into a patient, blood from the patient may flow out the rearward end of the catheter. Typically, once the catheter is attached to a fluid reservoir, such as an IV bag, the fluid pressure from fluid in the IV bag is sufficient to prevent or limit the flow of blood from the patient through the catheter. However, until the IV bag is connected to the catheter, blood may leak out the catheter. Therefore, it is desirable to plug the catheter to prevent blood leakage after the catheter is inserted into a patient.

Accordingly, preferably, the nose 22 forms a fluid-tight seal with the interior of the catheter hub 72 when the catheter is mounted on the nose. In this way, after the catheter is removed from the housing and the needle is retracted, the nose can be inserted into the catheter to plug the catheter. Further, referring to FIG. 3, preferably the nose extends forward of the follower portion 46 of the needle retainer 40 so that the nose 22 substantially plugs the catheter immediately after the needle is retracted. In addition, since the nose 22 projects forward of the follower portion 46, the needle is never exposed during and after retraction.

Configured as described above, the device operates as follows. Prior to use, the needle 30 is disposed in the projecting position so that the sharpened tip of the needle is exposed. The sharpened tip of the needle is inserted into a vein of a patient. Blood flowing into the flashback chamber 50 indicates to the medical professional that the needle is inserted into a vein. The catheter 70 is then threaded into the patient's vein by advancing the catheter to remove the catheter from the device 10. For this purpose, preferably, the catheter hub 72 includes a protrusion 73 that the medical professional can push forward with one of the fingers of the hand holding the device. When the catheter is advanced forward of the follower portion 46 of the needle retainer 40, the needle retainer 40 deflects inwardly so that the needle is released. The spring 60 then propels the needle 30, the needle retainer 40 and the flashback chamber 50 rearwardly so that the sharpened tip of the needle is enclosed within the housing 20. If the medical profession desires to do so, the nose 22 can then be inserted into the catheter to replug the catheter to prevent blood leakage.

Referring now, to FIGS. 5-7 an alternative embodiment is illustrated. Elements in the second embodiment that are similar to elements of the first embodiment illustrated in FIGS. 1-4 and described above are designated with like reference numbers, with the addition of 100s thereto.

The second embodiment is designated generally 110. The device 110 includes a housing 120, a retractable needle 130, a spring 160 biasing the needle rearwardly, and a needle retainer 140 releasably retaining the needle against the bias of the spring. An over-the-needle catheter 170 is mounted on the forward end of the device 110. The needle retainer 140 cooperates with the catheter so that upon removing the catheter from the device 110, the needle is released, and the spring propels the needle rearwardly into the housing 120.

The needle retainer 140 is configured similarly to the needle retainer 40 described in connection with the first embodiment. The needle retainer comprises an elongated resiliently flexible arm fixedly connected with the needle 30. The forward end of the needle retainer projects through an opening at the forward end of the housing adjacent the tip 122. The forward portion 146 of the needle retainer engages the side of the catheter hub 172. Similar to the first embodiment, the catheter hub 172 wedges the needle retainer arm radially outwardly so that a ridge 145 on the arm engages a lip 124 formed by the opening at the forward end of the housing. Accordingly, when the catheter 170 is removed from the device 110, the needle retainer 140 deflects inwardly to release the needle 30. The spring then propels the needle rearwardly into the housing 120. As shown in FIG. 7, the housing is elongated so that the entire length of the needle and the flashback chamber is enclosed within the housing in the retracted position.

In this way, as with the first embodiment, the needle automatically retracts after use so that the medical professional need not perform any additional steps to ensure that the contaminated needle is safely enclosed. The step of inserting the catheter 170 into the patient is sufficient to effectuate retraction. However, as discussed further below, the medical professional may delay retraction if desired.

It may be desirable to allow the medical professional to delay retraction after the catheter is inserted into the patient. Therefore, the device 110 includes a window 121 in the side of the housing 120. The needle retainer 140 is disposed adjacent the window allowing the medical professional to manually engage the needle retainer. If the medical professional desires to control retraction, the medical professional can apply pressure to deflect the needle retainer radially inwardly so that the retainer abuts an interior wall 125. In this way, the needle retainer is pinched between the grip of the medical professional and the interior wall to prevent the needle from retracting into the housing. Once the medical professional releases the needle retainer, the needle retracts into the housing.

Preferably, the window 121 is located so that the medical professional engages the needle retainer when grasping the device 110 for use. For this reason, preferably, a gripping portion is formed at the forward end of the housing. The gripping portion is formed by a pair of opposing concavely curved surfaces along the sides of the housing. The window 121 is formed in one of the opposing curved surfaces of the gripping portion.

The device operates as follows. Prior to use, the needle projects forwardly from the housing as shown in FIG. 5. The medical professional grasps the gripping portion of the housing to hold the device 110. In doing so, the medical professional engages the needle retainer through the window 121. The needle 130 is inserted intravenously into a patient. Once blood flow is detected in the flashback chamber 150, the catheter is axially advanced to insert the catheter into the patient. Once the catheter is axially advanced forward of the needle retainer, the needle is freed to retract except for the force being applied to the needle retainer by the medical professional. If the medical professional does not want to delay retraction the medical professional can release the finger pressure on the needle retainer so that the bias of the spring overcomes the finger pressure. Alternatively, the medical professional can delay retraction by maintaining his or her grip with sufficient force to overcome the bias of the spring 160. Once the medical professional releases the device, the needle automatically retracts into the housing so that the sharpened tip of the housing is enclosed. In this way, the needle automatically retracts after the device is used, and without any additional step, such as depressing a button. At the same time, if the medical professional desires to control retraction by delaying retraction, he or she may do so, without performing any additional steps. The natural steps of using the device allow such control. However, even if the medical professional desires to delay the retraction, the needle will eventually automatically retract without any further operation once the medical professional releases his or her grip on the device.

The device 110 also includes an adjustable nose piece 22. In the first embodiment, the nose 22 is integrally formed with the housing. In the second embodiment, the nose is a separate piece that is inserted into a socket at the forward end of the housing that is formed to receive the nose piece. The nose piece 122 may be axially adjusted relative to the housing 120. By adjusting the axial position of the nose piece, the length of the exposed sharpened needle tip projecting from the catheter cannula can be varied.

Referring now to FIGS. 8-10 generally and to FIG. 8 specifically, a device for introducing a guide wire 270 into a patient is designated generally 210. The device includes a needle 240 for piercing a vein of the patient. The guide wire is inserted into the patient's vein through the needle. After the guide wire is inserted into the patient, the insertion needle automatically retracts to that the contaminated needle is beyond the reach of the medical professional using the device. In addition, the medical professional using the device can control retraction of the device to delay retraction if desired. However, even if retraction is delayed, retraction occurs automatically once the medical professional puts the device down.

As shown in FIG. 8, the device includes a housing 220 having a reduced diameter tip 224. The needle 240 projects forwardly through an opening in the tip 224. The rearward end of the housing 220 is generally closed, having a reduced diameter opening through which the guide wire 270 enters the interior of the housing. A rubber seal 280 is disposed in the rearward end of the housing. The guide wire 270 extends through a hole in the seal, forming a fluid-tight seal with the seal 280. In addition, seal 80 frictionally engages the guide wire to frictionally connect the guide wire to the housing 220.

Rearward of the tip 224, the housing has a gripping area 222 formed of a plurality of raised ridges. During ordinary operation, the user grasps the gripping area to hold the device during insertion of the guide wire.

A spring 260 circumscribes the needle, biasing the needle 240 rearwardly toward a retracted position. A needle retainer 230 releasably retains the needle in the projecting position, in which the needle projects forwardly from the housing, as shown in FIG. 8. The needle retainer 230 comprises an elongated arm 232 that is pivotally connected to the housing 220 by a pivot pin 233 that forms the pivot axis for the motion of the needle retainer. A latch 235 is integrally formed on the arm 232 on the end of the arm remote from the pivot pin 233. The latch 235 projects into the interior of the housing.

Referring now to FIG. 9, the latch 235 engages a flash back chamber 250 that is affixed to the rearward end of the needle 240. The flashback chamber is a generally cylindrical hollow chamber. The rearward end of the needle has a side port 242 so that when the needle pierces the patient's vein, blood flows through the side port and into the flashback chamber to indicate to the medical professional that the vein has been pierced. Prior to advancing the guide wire 270, the guide wire projects into the needle 240 so that the forward end of the guide wire is rearward of the side port 242 in the needle. In this way, the guide wire seals the rearward end of the needle to prevent blood from leaking out the rearward end of the flashback chamber. At the same time, the guide wire does not block the side port so that blood can flow through the needle and into the flashback chamber.

The forward end of the flashback chamber 250 is sealed by a porous vent that is air permeable, but does not allow passage of blood from the flashback chamber. The rearward end of the flashback chamber is generally closed, having a small opening for receiving the guide wire 270. The guide wire passes through the rearward opening and into the needle. In this way, the guide wire seals the opening in the rear of the flashback chamber to prevent blood from leaking out of the flashback chamber.

As described above, the needle retainer pivots between a latched position in which the needle retainer retains the needle in the projecting position against the rearward bias of the spring, and an unlatched position in which the needle retainer releases the needle, allowing the spring to propel the needle rearwardly into the housing so that the sharpened end of the needle is enclosed. The needle retainer 230 automatically pivots from the latched position to the unlatched position after the guide wire 270 is inserted into the patient. The guide wire 270 prevents the needle retainer from pivoting into the unlatched position until the guide wire is inserted into the patient.

Specifically, a passageway 236 extends through the latch 235 for receiving the guide wire. The guide wire 270 projects through the latch passageway 236 and into the flashback chamber as shown in FIG. 10. While the guide wire resides within the latch passageway, the latch is prevented from pivoting into the unlatched position. When the rearward end of the guide wire 270 is displaced forwardly of the passageway so that the guide wire is removed from the passageway, the guide wire no longer retains the latch against being displaced radially outwardly. The rearward bias of the spring 260 urges the needle and attached flashback chamber rearwardly. This in turn urges the latch radially outwardly, so that the arm 232 pivots radially outwardly away from the needle. The spring then propels the needle into the housing 220 as shown in FIG. 10.

As mentioned previously, the medical professional operating the device 210, can optionally intervene to delay retraction. Specifically, as shown in FIG. 8, in the latched position the needle retainer 230 resides within a slot in the gripping portion. In this way, when the medical professional grasps the gripping portion 222, the medical professional also grasps the arm 232 of the needle retainer. As long as the medical professional grasps the needle retainer, the needle retainer will not pivot into the unlatched position. In this way, the medical professional can delay retraction after the guide wire is inserted into the patient. However, as soon as the medical professional releases the needle retainer 230, the needle retainer will pivot into the unlatched position and the spring will propel the needle into the retracted position.

Configured in this way, the device operates as follows. The needle 240 is inserted into a patient. Blood flowing into the flashback chamber provides a visual indication that the needle has been inserted into a vein. The medical professional then advances the guide wire 270 through the needle to insert the guide wire into the patient's vein. As the guide wire is advanced, the guide wire passes through the passage 236 that extends through the latch 235. Once the guide wire 270 is advanced forward of the latch, the needle retainer pivots into the unlatched position and the spring propels the needle rearwardly into the housing 220. If the medical professional desires to delay retraction, the medical professional grasps the needle retainer prior to advancing the guide wire forwardly of the latch. The guide wire is then advanced forwardly of the latch while the medical professional continues to grasp the needle retainer. When the medical professional desires to retract the needle, the medical professional needle simply releases his or her grip on the needle retainer. The spring then automatically propels the needle rearwardly into the retracted position.

Referring now to FIGS. 11-12, a second embodiment of a device for introducing a guidewire 370 into a patient is designated generally 310. The device includes a needle 340 for piercing a vein of the patient. The guidewire 370 is inserted into the patient's vein through the needle. After the guidewire is inserted into the patient, the insertion needle automatically retracts into the housing 320 so that the contaminated needle is beyond the reach of the medical professional using the device. In addition, the medical professional using the device can control retraction of the device to delay retraction if desired. However, even if retraction is delayed, retraction occurs automatically once the medical professional puts the device down.

The guidewire 370 is preferably a substantially inextensible semi-flexible wire. The forward end of the guidewire is rounded, and preferably the wire is solid. The wire is sized so that the diameter of the wire is slightly smaller than the interior bore of the needle 340 so that the wire is slidable within the needle.

The device includes a hollow housing or barrel 320. The needle 340 projects forwardly through an opening in the forward end of the housing 340. The rearward end of the housing 320 is generally closed, having a reduced diameter opening through which the guidewire 370 enters the interior of the housing. A rubber seal 380 is disposed in the rear of the housing. The guidewire 370 extends through a hole in the seal 380, forming a fluid-tight seal with the rubber seal. In addition, the seal 380 frictionally engages the guidewire to frictionally connect the guidewire to the housing 320.

A spring 360 circumscribes the needle, biasing the needle 340 rearwardly toward a retracted position, shown in FIG. 12. A needle retainer 30 releasably retains the needle in the projecting position, in which the needle projects forwardly from the housing, as shown in FIG. 11. The needle retainer 330 is an elongated arm integrally formed from the housing, so that the arm 330 and the housing 320 are formed of a one-piece construction. The arm 330 is formed so that the arm is biased radially outwardly toward the position illustrated in FIG. 12.

As shown in FIG. 11, prior to use the arm 330 projects into the interior of the housing 320. The forward end of the arm 330 forms a latch 335 that engages a flashback chamber 350 fixed to the rearward end of the needle 340. The flashback chamber 350 is a generally cylindrical hollow chamber. The rearward end of the needle has a side port 342 so that when the needle pierces the patient's vein, blood flows through the side port and into the flashback chamber to indicate to the medical professional that the vein has been pierced. Prior to advancing the guidewire 370, the guidewire projects into the needle 340 so that the forward end of the guidewire is rearward of the side port 342 in the needle. In this way, the guidewire seals the rearward end of the needle to prevent blood from leaking out the rearward end of the flashback chamber. At the same time, the guidewire does not block the side port so that blood can flow through the needle and into the flashback chamber.

The forward end of the flashback chamber 350 is sealed by a porous event that is here permeable, but does not allow passage of blood from the flashback chamber. The rearward end of the flashback chamber is generally closed, having a small opening for receiving the guidewire 370. The guidewire passes through the rearward opening and into the needle. In this way, the guidewire seals the opening in the rear of the flashback chamber to prevent blood from leaking out of the flashback chamber.

As described above, the needle retainer pivots between a latched position in which the needle retainer retains the needle in the projecting position against the rearward bias of the spring 360, and an unlatched position in which the needle retainer releases the needle, allowing the spring to propel the needle rearwardly into the housing so that the sharpened end of the needle is enclosed. The needle retainer 330 automatically pivots from the latched position to the unlatched position after the guidewire 370 is threaded into the patient. The guidewire 370 prevent the needle retainer from pivoting into the unlatched position until the guidewire is threaded into the patient.

Specifically, the arm 330 includes a forward wire passageway 332 and a rearward wire passageway 334 for receiving the guidewire 370. The passageways 332,334 are located and oriented so that when the arm 330 is disposed in the latched position, illustrated in FIG. 11, the passageways 332,334 are substantially co-axial with the needle 340. In this way, the guidewire 370 engages the needle retainer arm 330 to releasably retain the arm in the latched position, thereby releasably retaining the needle 340 in the projecting position against the bias of the spring 360. While the guidewire 370 resides within one of the latch passageways 332,334, the arm is prevented from pivoting into the unlatched position. When the rearward end of the guidewire 370 is displaced forwardly of the forward wire passageway 332 so that the guidewire is removed from the passageway, the guidewire no longer retains the arm against being displaced radially outwardly. The rearward bias of the spring 60 urges the needle 340 and attached flashback chamber 350 rearwardly. This, along with the radial bias of the arm 330 urges the arm radially outwardly, so that the arm pivots radially outwardly away from the needle. The spring then propels the needle into the housing 320 as shown in FIG. 12.

As shown in FIG. 11, preferably the arm 330 is bent to form a trough or depression. Preferably, the top surface of the trough is vertically spaced below the center line or axis of the needle 340. As shown in FIG. 11, a portion of the guidewire 370 between the wire passageways 332,334 is external of the housing 322 and exposed for manual manipulation by the medical professional. In this way, the medical professional can both hold the device and feed the guidewire 370 into the patient with one hand. Specifically, while holding the device 310 with one hand, the medical professional can engage the exposed portion of the wire between the passageways 332, 334 and displace the guidewire forwardly to thread the guidewire through the needle 340 and into the patient.

Referring now to FIGS. 13-17 in general and to FIG. 13 specifically, there is shown a catheter insertion device 410 for inserting a catheter 450 into a patient. The device 410 has a needle 420 to guide the catheter 450 into a vessel of the patient. The insertion device 410 is adapted to automatically retract the needle 420 inside the insertion device 410 when the operator removes the catheter 450 from the device. In addition, the device is configured to allow the operator to delay the retraction. These features allow the operator to control retraction, while ensuring that the needle automatically retracts after use to render the needle non-reusable and safely disposable.

The catheter insertion device 410 includes a generally cylindrical hollow barrel or housing 430 having a reduced diameter forward tip portion 434. The needle 420 is releasably retained so that the forward end of the needle projects forwardly through a hole in the barrel tip 434. The needle is operable between an extended position and a retracted position. In the retracted position, the needle is enclosed within the housing.

The catheter 450 is initially mounted on the forward end of the catheter insertion device 410 with the needle 420 projecting from the front of the device through the catheter. The catheter 450 comprises a cannula 452 and a hub 454. The cannula 452 sheaths or receives the front portion of needle 420, so that the sharpened point of the needle extends slightly beyond the open end of the cannula.

The catheter 450 includes a flexible, elongated cannula 452 attached to the catheter hub 454. The cannula 452 telescopingly engages the needle so that the cannula sheaths the needle, with the sharpened tip of the needle 422 projecting beyond the forward end of the cannula. The rearward edge of the sharpened tip 422 is referred to as the heel of the needle bevel. The length of the needle between the heel of the needle bevel and the forward end of the cannula is referred to as the lie length. Preferably, the lie length is adjustable.

In the present instance, the lie length is adjustable by maintaining the extended position of the needle constant, and adjusting the position of the catheter 450 when the catheter is mounted on the barrel prior to use. The tip of the barrel 420 is adjustable to provide for adjustment of the catheter.

Referring now to FIG. 15, the barrel 420 includes a displaceable tip 434. In the present instance, the tip 434 is a separate component that is inserted into an opening at the forward end of the barrel 430. The tip 434 includes an external circumferential flange 439 against which the rearward edge 455 of the catheter hub 454 seats. Therefore, varying the axial position of the tip 434 adjusts the axial position of the flange 439 thereby adjusting the lie length.

The tip 434 includes a generally cylindrical rearward portion having an external diameter that is slightly less than the internal diameter of the forward portion of the barrel 430. A plurality of barbs 438 project from the external surface of rearward end of the tip 434. The barbs 438 engage the internal surface of the barrel 430 to connect the tip 434 to the barrel. The axial position of the flange 439 is determined by the distance that the rearward end of the tip is inserted into barrel 430. By adjusting the amount the tip is inserted, the axial position of the flange 439 is adjusted, thereby adjusting the lie length.

As shown in FIG. 15, a generally cylindrical chamber 470 is attached to the rearward end of the needle. The chamber 470 forms a flashback chamber. The flashback chamber 470 is attached to the rearward end of the needle 420 so that the flashback chamber encloses the rearward end of the needle 420. The rearward end of the flashback chamber is closed by a porous vent plug 472. The vent plug 472 allows the passage of air out of the chamber 470, while preventing blood from escaping from the flashback chamber 470.

The needle 420 is biased rearwardly toward its retracted position by a biasing element 460. In the present instance, the biasing element is a coil spring 460 that surrounds the needle. The forward end of the spring 460 bears against an internal shoulder formed in the tip 434. The rearward end of the spring bears against the flashback chamber 470, biasing the flashback chamber and the attached needle rearwardly. Alternatively, the spring 60 may be connected to the needle by an adhesive, such as epoxy. The needle 420 and flashback chamber 470 are releasably retained against the bias of the spring 460 by a needle retainer or lever arm 440 that is pivotally connected to the housing 430.

The needle retainer 440 has a forward portion 444 and a rearward portion 448. In the present instance, the forward portion 444 extends in the forward direction from a pivot 442, and the rearward portion 48 extends rearwardly from the pivot 442. The interior surface of the forward portion 444 of the retainer 440 abuts with the hub 454 of the catheter 450 when the catheter is mounted on the insertion device 410. Preferably, the forward portion 444 of the retainer 440 abuts or engages the external surface of the catheter hub 454. Alternatively, the forward portion may engage the internal surface of the catheter hub 454. The rearward portion 448 of the needle retainer 440 is located rearwardly from the pivot point and catheter 450, when the catheter is mounted on the insertion device.

The rearward portion 448 of the needle retainer 440 comprises a release lever having a latch 446 formed thereon. The lever is pivotable between a locked position and an unlocked position. In the locked position, the release lever extends generally parallel to the longitudinal axis of the device 410. The latch 446 on the end of the release lever passes through an opening 432 in the side of the barrel 430, so that the rear end of the flashback chamber 470 abuts the latch to retain the needle in its extended position.

It is desirable to align the sharpened tip 422 of the needle 420 so that the bevel of the sharpened tip is circumferentially located relative to the barrel 430, as illustrated in FIG. 13. Specifically, preferably, the sharpened tip is circumferentially located so that the forward-most point of the sharpened tip is vertically positioned below the heel of the tip bevel. In the present instance, the flashback chamber 470 is configured to cooperate with needle retainer to facilitate aligning the bevel of the needle, as described below.

The flashback chamber 470 is generally cylindrical, and includes a flat surface extending along the length of the flashback chamber. The desired circumferential orientation of the needle bevel is located relative to the flat on the flashback chamber when the flashback chamber is connected to the needle. Referring to FIG. 15, the rearward portion 448 of the needle retainer includes a generally planar surface or ledge 449 that cooperates with the flashback chamber 470 to circumferentially align the needle 420 relative to the barrel 430. As shown in FIG. 15, when the needle retainer 440 is disposed in the latched position, the flat on the flashback chamber 470 is aligned with and engages the ledge 449 of the needle retainer. In this way, the flashback chamber 470 and the attached needle 420 are circumferentially located relative to the needle retainer, and in turn to the barrel 430.

The engagement between the forward portion 444 of the needle retainer lever and the catheter hub 454 prevents the lever from pivoting to its unlocked position when the catheter is mounted on the insertion device. The rear portion 48 of the retainer 440 is preferably biased to pivot away from the side of the housing 430. In the present instance, the face of the latch 446 that engages the flashback chamber 470 is angled so that a portion of the rearward bias of spring 460 is transferred to the lever biasing the lever radially outwardly. After the catheter 450 is removed past the end of the lever, the retainer is free to pivot into its unlocked position, thus moving the latch 446 out of engagement with the rear end of the needle 420. The spring 460 then propels the needle rearwardly into the housing 430.

The operator can control retraction of the needle, if desired, as follows. The needle retainer 440 includes a rib 445 that is transverse the longitudinal axis of the needle retainer lever. As shown in FIGS. 13 and 14, the barrel 430 includes a gripping portion comprised of a plurality of parallel spaced apart ribs 431. The needle retainer rib 445 is generally parallel to the gripping ribs 431 so that the needle retainer rib 445 forms part of the gripping portion. In this way, if the operator desires to control retraction of the needle, the operator grasps the rib 445 of the needle retainer when grasping the gripping portion of the device 410.

By grasping the needle retainer rib 445, the operator impedes pivoting of the needle retainer 440 from the locked position to the unlocked position. After the operator inserts the catheter 450 into the patient, the forward portion 444 of the needle retainer is disengaged from the catheter, thereby allowing the needle retainer to pivot toward the unlocked position. However, the operator's grasp of the needle retainer rib 445 operates as an override preventing the needle retainer from pivoting into the unlocked position. The operator can control retraction by maintaining an inward force on the needle retainer rib 445 until retraction is desired. Once the operator releases the needle retain rib 445 after the catheter 450 has been disengaged from the needle retainer 440, the needle retainer is free to pivot into the unlocked position so that the spring 460 propels the needle 420 rearwardly into the barrel 430. In this way, the device prevents retraction from occurring until after the catheter 450 is disengaged from the housing of the insertion device. In addition, the device allows the operator to control the timing of retraction, while ensuring that retraction occurs after use of the device.

The catheter insertion device is initially provided in the configuration shown in FIG. 13. The operator of the catheter insertion device 410 first uses the needle point 422 to pierce a blood vessel of the patient. When the needle point 422 pierces the patient's blood vessel, blood flows through the needle 420 and collects in the transparent flashback chamber 470. The appearance of blood in the flashback chamber 470 serves as a visible indication to the operator that a blood vessel has been appropriately pierced, and that the catheter 450 is properly positioned. The operator then slides the catheter hub 454 off of the forward end of the device 410, in the direction of the pointed end 422 of the needle 420, to insert the catheter lumen 452 into the patient's blood vessel. This motion of removing the catheter hub 454 from the device causes the retainer 440 to automatically pivot out of contact with the end of the needle when the rim 455 of the catheter hub passes the end of lever 444. However, the operator can temporarily override the automatic retraction by grasping the needle retainer rib 445 prior to removing the catheter hub. Once the operator releases the needle retainer rib 445, the needle retainer pivots out of engagement with the needle 420. The needle is thereby released and withdrawn into the barrel 430 of the catheter insertion device 410 under the bias of spring 460. The operator need not perform any additional action to effectuate retraction of the needle other than that required by a normal catheter insertion procedure. At the same time, the operator can intervene to delay retraction, if desired.

Referring to FIG. 15, the tip 434 further includes a constricted portion 435 having an internal diameter slightly larger than the external diameter of the needle 420. The close fit between the constricted portion 435 and the needle limits leakage of blood into the barrel 430 during a replugging step, as described further below. In addition, an external circumferential rib 437 protrudes radially from the front end of the tip 434. The rib 437 cooperates with the internal cavity of the catheter hub 454 to provide a fluid-tight seal. The internal cavity is tapered, having a major diameter that is greater than the diameter of the rib 437 on the tip 434. Preferably, a substantially cylindrical zero draft zone is formed at the forward-most portion of the internal cavity. The zero draft zone has an internal diameter that is similar to the external diameter of the rib 437 on the tip 434. In this way, when the catheter 450 is mounted on the barrel 430, the rib 437 engages the zero draft zone to form a fluid-tight seal.

After the catheter has been inserted into the patient and the needle 420 has been retracted, the tip 434 of the device can be inserted into the catheter 450 to replug the catheter to prevent blood from leaking out of the catheter. For this reason, the catheter 450 and/or the forward end of the needle retainer 440 are configured to facilitate pivoting of the needle retainer so that the forward end of the needle retainer does not interfere with replugging of the catheter. Specifically, the forward edge of the needle retainer is rounded so that the forward portion 444 of the needle retainer 440 pivots downwardly from the perspective of FIGS. 13 and 15 when the needle retainer engages the rim 455 of the catheter 450. Alternatively, the rim 455 can be rounded or tapered to facilitate pivoting of the needle retainer 440 upon forward axial displacement of the tip 434 relative to the catheter 450 after the catheter has been removed from the device a sufficient amount to disengage the needle retainer from the needle 420.

The catheter 450 is replugged after retraction by inserting the tip 434 of the barrel 430 into the catheter cavity so that the circumferential rib 437 engages the zero draft zone. The rib 437 and the zero draft zone cooperate to form a fluid-tight seal so that blood does not leak from the catheter around the tip 434. In addition, the retracted needle 420 forms a seal with the constricted portion 435 of the tip 434 to reduce or eliminate blood leakage from the catheter 450 into the barrel 430. In the retracted position, the latch 446 deflects and/or deforms the needle.

The tip 434 further includes an external circumferential depression or recess 436. Initially, the catheter 450 encloses the tip 434 so that the operator cannot see the recess 436. As the operator removes the catheter 450 from the tip 434, the recess 436 is uncovered so that the operator can see the recess. After the recess 436 is uncovered, continued removal of the catheter 450 displaces the catheter beyond the forward end of the needle retainer 440, so that the needle retainer pivots into the unlatched position. In this way, the recess operates as a visual indicator to the operator, providing a visual signal that continued forward displacement of the catheter will cause needle retraction. Preferably, the recess 436 is textured to enhance the visual distinction between the recess and the rest of the external surface of the tip. Alternatively, a different visual indicator can be provided, such as a circumferential colored line located on the tip 434 axially rearwardly of the forward end of the needle retainer 440.

Referring now to FIGS. 18-20, there is shown another embodiment of a catheter insertion device 510. The alternate embodiment shown in FIGS. 17-20 incorporates elements that are similar to elements in the embodiment described above in connection with FIGS. 13-17. Parts in FIGS. 18-20 that are similar to the parts in FIGS. 13-17 are numbered by the same number designator with the addition of 500's thereto.

The catheter insertion device 510 includes an insertion needle 520 projecting forwardly from a barrel or housing 530. The needle 520 is releasably retained by a needle retainer 540 comprising a release lever. The needle retainer 540 engages a catheter 550 mounted on the tip 534 of the housing 530. In this manner, the catheter 550 impedes pivoting of the needle retainer 540 and prevents retraction of the needle 520 while the catheter is mounted on the housing 530 of the device 510.

As in the embodiment described above in connection with FIGS. 13-17, the catheter insertion device 510 in FIG. 18 is also operable to automatically retract the needle without manual intervention or requiring a separate step for retraction. The needle retainer 540 is biased toward an unlatched position, so that when the catheter 550 is removed from the insertion device 510, the needle retainer 540 automatically pivots into its unlatched position, releasing the needle 520. The spring 560 then propels the needle 520 rearwardly into the housing 530, so that the sharpened tip of the needle 520 is safely enclosed within the housing.

In addition, as in the previous embodiment, the device 510 includes an exposed, manually actuable surface that allows the operator to intervene to delay retraction if desired. Specifically, the device includes a control button 580 that engages a pawl 549 connected to the needle retainer 540. The control button 580 operates between a locked position and an unlocked position. In the locked position the control button engages the pawl 549 on the needle retainer 540 preventing the needle retainer from pivoting into the unlatched position to release the needle 520. The control button is displaceable toward the unlocked position, which corresponds to the needle retainer 540 being in the unlatched position.

The control button 580 and pawl 549 have mating tapered surfaces. When the needle retainer 540 pivots, the mating tapered surfaces of the pawl and control button transfers a vertical force to the button, displacing the control button upwardly into the unlocked position. Accordingly, absent operator intervention, when the catheter 550 is removed from the housing 530, the needle retainer 540 pivots into the unlatched position, displacing the control button into the unlocked position. The needle then retracts into the housing.

The operator can intervene to delay retraction by depressing the control button 580 before the catheter is removed. The downward force applied by the operator on the control button locks the pawl 549 in place, preventing the needle retainer from pivoting. After the catheter is removed from the housing, the needle retainer retains the needle as long as the operator depresses the control button. As soon as the operator releases the control button, the pawl is free to rotate, so that the needle retainer pivots into the unlatched position and the needle retracts. In this way, retraction of the insertion needle occurs automatically after the device is used, but the operator can delay retraction if desired.

The device 510 also illustrates an alternate arrangement for the flashback chamber 520. The flashback chamber 520 can be configured as in the previous embodiment in which the flashback chamber 470 encloses the rearward open end of the needle 420, and the needle retainer 440 engages the flashback chamber. Alternatively, in the present embodiment, the rearward end of the needle 520 projects rearwardly from the flashback chamber 570, and the needle retainer 540 engages the rearward end of the needle. The rearward end of the needle is plugged to prevent blood from leaking into the housing. In addition, a side port is formed in the side of the needle, and the flashback chamber encloses the side port. Blood from the patient flows through the side port and into the flashback chamber, serving as a visual indicator that the patient's artery has been pierced.

Referring now to FIGS. 22-25, there is shown yet another alternative embodiment of a catheter insertion device 610. The device 610 incorporates elements that are similar to devices previously described and illustrated in FIGS. 13-21. Such elements are designated with the same number designations with the addition of 600's thereto.

The catheter insertion device 610 includes an insertion needle 620 projecting forwardly from a barrel or housing 630. The needle 620 is releasably retained by a pivotable needle retainer 640 comprising a release lever. One end of the needle retainer 640 engages a catheter 650 mounted on the tip 634 of the housing 630. In this arrangement, the catheter 650 impedes the needle retainer 640 from releasing the needle 620 while the catheter is mounted on the housing 630 under the retainer 640.

As in the embodiments described above in connection with FIGS. 13-21, the catheter insertion device 610 in FIG. 22 is also operable to automatically retract the needle without manual intervention or requiring a separate step for retraction. The needle retainer 640 is biased toward an unlatched position, so that when the catheter 650 is removed from the insertion device 610, the needle retainer 640 automatically pivots into its unlatched position, releasing the needle 620. The spring 660 then propels the needle 620 rearwardly into the housing 630, so that the sharpened tip of the needle 620 is safely enclosed within the housing.

In addition, as in the previously described embodiments, the device 610 includes an exposed, manually actuable surface that allows the operator to intervene to delay retraction if desired. Specifically, the housing includes a gripping portion 691 providing a surface for the operator to grasp the device 610. The needle retainer 640 is located adjacent the gripping portion 631 so that the operator can readily engage the needle retainer to prevent the needle retainer from pivoting into the unlatched position.

Referring to FIGS. 22 and 23, the housing 630 includes the gripping portion 631, which is formed of a plurality of parallel spaced apart ribs. The ribs form a convex curved surface providing a secure anti-slip surface. As shown in FIG. 13, the housing may include opposing gripping surface for gripping the device. In the present instance, the barrel includes the gripping portion 631 on one side of the housing, and the rearward portion 648 of the needle retainer 640 is located on the other side of the housing, opposing the gripping portion. The exposed surface of the rearward portion 648 of the needle retainer 640 is configured and textured similar to the gripping portion 631. Accordingly, when the operator grasps the device for use, the operator's normal grip on the device operates to depress the rearward portion of the needle retainer. As long as the operator depresses the rearward portion of the needle retainer, the operator prevents the needle retainer from pivoting radially outwardly to release the needle for retraction.

The device 610 also includes a telescoping barrel to reduce the overall length of the housing prior to use. Alternatively, the device 610 can use a single piece housing as described above in the foregoing devices 410, 510.

The housing 630 of the device 610 comprises two components, an outer sleeve 690 and an inner sleeve 695. The inner sleeve 695 telescopes within the outer sleeve 690. Prior to use, the inner sleeve 695 is enclosed within the rearward end of the outer sleeve 690. When the needle 620 is retracted, the flashback chamber 670 and attached needle engages the inner sleeve, displacing the inner sleeve rearwardly as the needle retracts. In this way, the outer sleeve telescopes outwardly extending the length of the housing to accommodate the entire length of the needle.

The housing includes a forward stop to prevent the inner sleeve 695 from being reinserted into the outer sleeve 690. The housing further has a rearward stop to prevent the inner sleeve from being displaced rearwardly beyond the rearward edge of the outer sleeve.

A pair of resilient locking tabs 697 formed in the side of the inner sleeve 695 cooperates with the rearward edge of the outer sleeve 690 to operate as the forward stop. The locking tabs 697 are biased radially outwardly. When the inner sleeve 695 is enclosed within the outer sleeve 690, the locking tabs 697 engage the inner surface of the outer sleeve so that the locking tabs are substantially flush with the outer surface of the inner sleeve. When the inner sleeve is displaced rearwardly so that the locking tabs are rearward of the outer sleeve, the locking tabs flex radially outwardly as shown in FIGS. 23 and 24. Accordingly, attempts to displace the inner sleeve forwardly after retraction causes the locking tabs to engage the rear edge of the outer sleeve, thereby preventing forward displacement.

An annular lip 693 on the outer sleeve 690 cooperates with a circumferential flange 696 on the inner sleeve 695 to operate as the rearward stop. Referring to FIGS. 23 and 24, the annular lip 693 projects radially inwardly from the rearward edge of the outer sleeve 690. The circumferential flange 696 projects radially outwardly from the forward edge of the inner sleeve 695. When the inner sleeve is displaced rearwardly, the circumferential flange 696 engages the annular lip 693 impeding further rearward displacement of the inner sleeve.

The terms and expressions which have been employed are used as terms of description and not of limitation. There is no intention in the use of such terms and expressions of excluding any equivalents of the features shown and described or portions thereof. It is recognized, however, that various modifications are possible within the scope and spirit of the invention as defined by the appended the claims.

What is claimed is:

1. A method for inserting a guide wire into a patient, comprising the steps of:
providing a device having a housing, a needle, a biasing element biasing the needle rearwardly, a needle retainer for releasably retaining the needle so that the needle projects forwardly from the housing, and a guide wire operable to be inserted into a patient through the needle;
inserting the guide wire into the patient;
releasing the needle to allow the biasing element to retract the needle rearwardly;
selectively manually engaging the needle retainer to impede retraction of the needle; and
releasing the selective manual engagement with the needle retainer to release the needle so that the biasing element retracts the needle rearwardly.

2. A medical device comprising:
a hollow housing;
a needle having a sharpened tip operable between an extended position extending forwardly from the housing and a retracted position in which the needle is enclosed in the housing;
a needle hub connected to the needle;
a biasing element biasing the needle toward the retracted position;
a needle retainer integrally formed with the housing, the needle retainer releasably retaining the needle against the bias of the biasing element, wherein the needle retainer comprises a radially displaceable arm having a portion that releasably engages the needle hub; and
a guide wire projecting through the needle for insertion into a patient;
wherein substantially the entire length of the arm is displaced radially outwardly into an unlocked position to release the needle hub so that the biasing element displaces the needle rearwardly relative to the housing so that the sharpened tip is shielded within the housing against inadvertent contact.

3. The medical device of claim 2 wherein the needle is displaced rearwardly so that the sharpened tip is enclosed within the housing.

4. The medical device of claim 2 wherein the device is configured such that the guide wire can be inserted into the patient while the needle is inserted in the patient.

5. The medical device of claim 2 wherein the needle retainer is actuable by a simple unitary motion to effectuate retraction.

6. The medical device of claim 2 wherein the needle retainer cooperates with the guide wire such that disengaging the guide wire from the needle retainer causes the needle retainer to displace radially to move the portion of the arm that engages the needle hub out of its engagement with the needle hub.

7. The medical device of claim 2 wherein the needle retainer is configured to cooperate with both the guide wire and the needle hub.

8. The medical device of claim 2 wherein the needle hub is configured to urge the arm of the needle retainer radially outwardly when the needle hub moves rearwardly relative to the housing.

9. The medical device of claim 2 wherein the arm is accessible from an exterior of the housing such that the arm can be grasped during use of the medical device.

10. The medical device of claim 9 wherein the arm of the needle retainer is configured to delay displacement of the needle retainer into the unlocked position when the arm is grasped.

11. A medical device comprising:
a hollow housing;
a needle having a sharpened tip operable between an extended position extending forwardly from the housing and a retracted position in which the needle is enclosed in the housing;
a needle hub connected to the needle;
a biasing element biasing the needle toward the retracted position;

a needle retainer releasably retaining the needle against the bias of the biasing element, wherein the needle retainer comprises a radially deformable and displaceable arm having a portion that releasably engages the needle hub; and a guide wire projecting through the needle for insertion into a patient;

wherein substantially the entire length of the arm is displaced radially outwardly into an unlocked position to release the needle hub so that the biasing element displaces the needle rearwardly relative to the housing so that the sharpened tip is shielded within the housing against inadvertent contact.

12. A medical device comprising:

a hollow housing;

a needle having a sharpened tip operable between an extended position extending forwardly from the housing and a retracted position in which the needle is enclosed in the housing;

a needle hub connected to the needle;

a biasing element biasing the needle toward the retracted position;

a needle retainer releasably retaining the needle against the bias of the biasing element, wherein the needle retainer comprises a radially displaceable arm having a portion that releasably engages the needle hub; and a guide wire projecting through the needle for insertion into a patient;

wherein substantially the entire length of the arm is displaced radially outwardly into an unlocked position to release the needle hub so that the biasing element displaces the needle rearwardly relative to the housing so that the sharpened tip is shielded within the housing against inadvertent contact, wherein the needle retainer is cooperable with the guide wire, such that disengaging the guide wire from the needle retainer causes the needle retainer to be automatically displaced into the unlocked position.

13. A medical device comprising:

a hollow housing;

a needle having a sharpened tip operable between an extended position extending forwardly from the housing and a retracted position in which the needle is enclosed in the housing;

a needle hub connected to the needle;

a biasing element biasing the needle toward the retracted position;

a needle retainer releasably retaining the needle against the bias of the biasing element, wherein the needle retainer comprises a radially displaceable arm having a portion that releasably engaging a shoulder on engages the needle hub; and a guide wire projecting through the needle for insertion into a patient, wherein the needle retainer is cooperable with the guide wire, such that disengaging the guide wire from the needle retainer causes the needle retainer to be automatically displaced into an unlocked position;

wherein displacing the arm of the needle retainer radially outwardly into the unlocked position releases the needle hub so that the biasing element displaces the needle rearwardly relative to the housing so that the sharpened tip is shielded within the housing against inadvertent contact.

* * * * *